(12) United States Patent
Barshinger et al.

(10) Patent No.: US 7,263,888 B2
(45) Date of Patent: Sep. 4, 2007

(54) TWO DIMENSIONAL PHASED ARRAYS FOR VOLUMETRIC ULTRASONIC INSPECTION AND METHODS OF USE

(75) Inventors: James Norman Barshinger, Scotia, NY (US); Thomas James Batzinger, Burnt Hills, NY (US); Wei Li, Bothell, WA (US); John Broddus Deaton, Jr., Niskayuna, NY (US); David Paul Lappas, Hamilton, OH (US); Robert Snee Gilmore, Charlton, NY (US); Richard Eugene Klaassen, West Chester, OH (US); Michael John Danyluk, Waukesha, WI (US); Patrick Joseph Howard, Cincinnati, OH (US); David Charles Copley, Loveland, OH (US)

(73) Assignee: General Electric Company, Niskayuna, NY (US)

( * ) Notice: Subject to any disclaimer, the term of this patent is extended or adjusted under 35 U.S.C. 154(b) by 64 days.

(21) Appl. No.: 10/686,756

(22) Filed: Oct. 16, 2003

(65) Prior Publication Data

US 2005/0081636 A1 Apr. 21, 2005

(51) Int. Cl.
*G01N 9/24* (2006.01)
*G01N 29/00* (2006.01)
*G01N 29/04* (2006.01)
(52) U.S. Cl. .......................................... 73/606; 73/587
(58) Field of Classification Search .................. 73/606
See application file for complete search history.

(56) References Cited

U.S. PATENT DOCUMENTS 4,890,268 A 12/1989 Smith et al.
5,305,756 A 4/1994 Entrekin et al.
5,333,503 A * 8/1994 Hasegawa et al. ............ 73/642
5,481,918 A * 1/1996 Hasegawa et al. ............ 73/642
5,533,401 A 7/1996 Gilmore
5,677,491 A * 10/1997 Ishrak et al. .................. 73/641
6,089,096 A 7/2000 Alexandru (Continued)

FOREIGN PATENT DOCUMENTS

EP 0689187 12/1995

(Continued)

OTHER PUBLICATIONS

S. W. Smith et al., "High-Speed Ultrasound Volumetric Imaging System—Part I: Tranducer Design and Beam Steering," IEEE Transactions on Ultrasonics, Ferroelectrics and Frequency Control, vol. 38, No. 2, Mar. 1, 1999, pgs.

(Continued)

*Primary Examiner*—Hezron Williams
*Assistant Examiner*—Samir M. Shah
(74) *Attorney, Agent, or Firm*—Penny A. Clarke; Patrick K. Patnode (57) ABSTRACT

The present disclosure provides for the application of a two-dimensional ultrasonic phased array (100), formed of a plurality of transducers (102) arranged in a rectilinear pattern, for material and volumetric component testing. The two-dimensional array enables electronic adjustment of the focal properties and size of the aperture in both the azimuthal and elevational directions such that uniform and/or specified sound field characteristics can be obtained at any or all locations in the component being tested.

40 Claims, 5 Drawing Sheets

U.S. PATENT DOCUMENTS

| | | |
|---|---|---|
| 6,464,638 B1 | 10/2002 | Adams et al. |
| 6,789,427 B2 * | 9/2004 | Batzinger et al. ............. 73/614 |
| 2004/0050166 A1 * | 3/2004 | Batzinger et al. ............. 73/614 |

FOREIGN PATENT DOCUMENTS

JP    2004141447 A  *  5/2004

OTHER PUBLICATIONS

D. H. Turnbull et al., "Beam Steering With Pulsed Two-Dimensional Transducer Arrays," IEEE Transactions on Ultraconics. Ferroelectrics and Frequency Control, vol. 38, No. 4, Jul. 1, 1999, pp. 320-333.

EP Search Report, EP 04 25 6351, Jan. 26, 2005, E. Uttenthaler.

* cited by examiner

TWO DIMENSIONAL PHASED ARRAYS FOR VOLUMETRIC ULTRASONIC INSPECTION AND METHODS OF USE

BACKGROUND

The present invention relates to phased array ultrasonic inspection, and more particularly to a novel two dimensional phased array transducer and inspection method for the non-destructive evaluation of the volume of a material or test piece using focused ultrasonic beams.

When inspecting and/or testing materials which produce a degree of back scattering, such as, for example, titanium, steel or nickel-base super alloys, focusing of the ultrasonic inspection beam enhances the back-reflected signal from flaws contained in the test material and also reduces the noise produced by the test material. This improves the signal to noise ratio (SNR) for all ultrasonic indications, and in turn improves the capability of detecting flaws and the probability of detection (POD), allowing for the detection of flaws having reflectivities equivalent to #1 ($1/64$") or #2 ($2/64$") flat bottom holes. Such inspections are often required for aircraft materials, particularly those found in the rotating components of a jet engine.

However, in addition to these benefits, the reduction in insonified material volume also reduces the volume of test material that is interrogated by each ultrasonic pulse. Therefore, many focused interrogating pulses are required to inspect the volume of material under test. The conventional ultrasonic solution involves a mechanical scanning system using a series of single elements, spherically focused probes, each focused at a different depth in the material and spaced such that each individual probe setup produces a focal zone that slightly overlaps the next to produce a uniform insonification over the entire depth of interest. Each of these individual zone setups is then scanned over the surface of the material to finally produce a three dimensional volume of data for the test object. This technique is generally referred to as a "multizone" inspection and is described in U.S. Pat. No. 5,533,401A.

The primary drawback to such a technique is the time involved in setting up and scanning the entire set of zones for the given volume of material under test. An additional drawback is the difficulty in accommodating for surface curvature or other complex geometry on the surface of the test piece. This will typically require the use of either custom transducers, or complex mirror arrangements to produce the desired focal characteristics in the material. Thus, it is desirable to increase the speed at which focused beams can scan in order to reduce the inspection times, while retaining the improvements in POD for critical flaws, and accommodating for surface curvature and complex geometry.

Phased arrays are recognized as having the ability to scan and manipulate focal properties in an electronic fashion and on a shot by shot basis, thus replacing the mechanical motion of a scanner and the fixed focus of a conventional transducer. Thus, it is conceivable to replace the multiple mechanical setups and multiple transducers of the multizone technique with a single phased array transducer, and achieve the ultimate goals of a reduced inspection time, and easy accommodation of surface geometry.

The ability of a phased array to produce a focused beam at a significant distance from that array is primarily dependent on its element configuration and the spatial extent of the array aperture with respect to the radiated wavelength. Since focusing cannot be accomplished in an aperture's far-field it is necessary to produce arrays that can place the inspection volumes well within an aperture's near-field if that inspection volume is to be interrogated by focused beams. Furthermore, in order to generate and manipulate focal geometries in a three dimensional sense within the volume of material it is necessary that the array elements be positioned in at least a two dimensional pattern. Large area two-dimensional arrays require large area elements and/or transducers to make up the array, since electronic design limitations tend to fix the number of elements and/or transducers that can be addressed and phased. These relatively large elements and/or transducers will in turn have directivity functions of their own which limit their ability to focus over a range of angles and therefore depths.

Accordingly, the need exists for unique array architectures and focusing lenses to achieve significantly large transducer apertures within the available state of the art beamforming capabilities.

BRIEF DESCRIPTION OF THE INVENTION

The present disclosure provides for the application of a two-dimensional ultrasonic phased array, formed of a plurality of transducers, for material and volumetric component testing. The two-dimensional array enables electronic adjustment of the size of the aperture in both the azimuthal and elevational directions such that uniform and/or specified sound field characteristics can be obtained at any or all locations in the component being tested.

According to one aspect, a two-dimensional ultrasonic phased array for inspecting a test material is provided. The two-dimensional phased array can include a plurality of ultrasonic elements arranged in a two-dimensional rectilinear grid pattern extending in an azimuthal and elevational direction, each ultrasonic element is individually addressable and controllable to manipulate the formation of a scanning beam in both the azimuthal and elevational directions and to produce focal characteristics throughout the volume of the test material. In one embodiment, the ultrasonic elements are transducers.

According to another aspect of the present disclosure, a method for performing a volumetric ultrasonic inspection of a test material is provided. The method includes the step of providing a two-dimensional ultrasonic phased array. The phased array includes a plurality of ultrasonic elements arranged in a two-dimensional rectilinear grid pattern extending in an azimuthal and elevational direction. The method further includes the steps of applying modulation to each of the ultrasonic elements to form a scanning beam, and interrogating at least a portion of the test material with the scanning beam.

BRIEF DESCRIPTION OF THE DRAWINGS

The above features and advantages of the present invention will become apparent from a study of the following detailed description taken in conjunction with the accompanying drawings, in which like reference numerals refer to like elements throughout the several views, and in which.

DETAILED DESCRIPTION OF THE INVENTION

Figure 1:
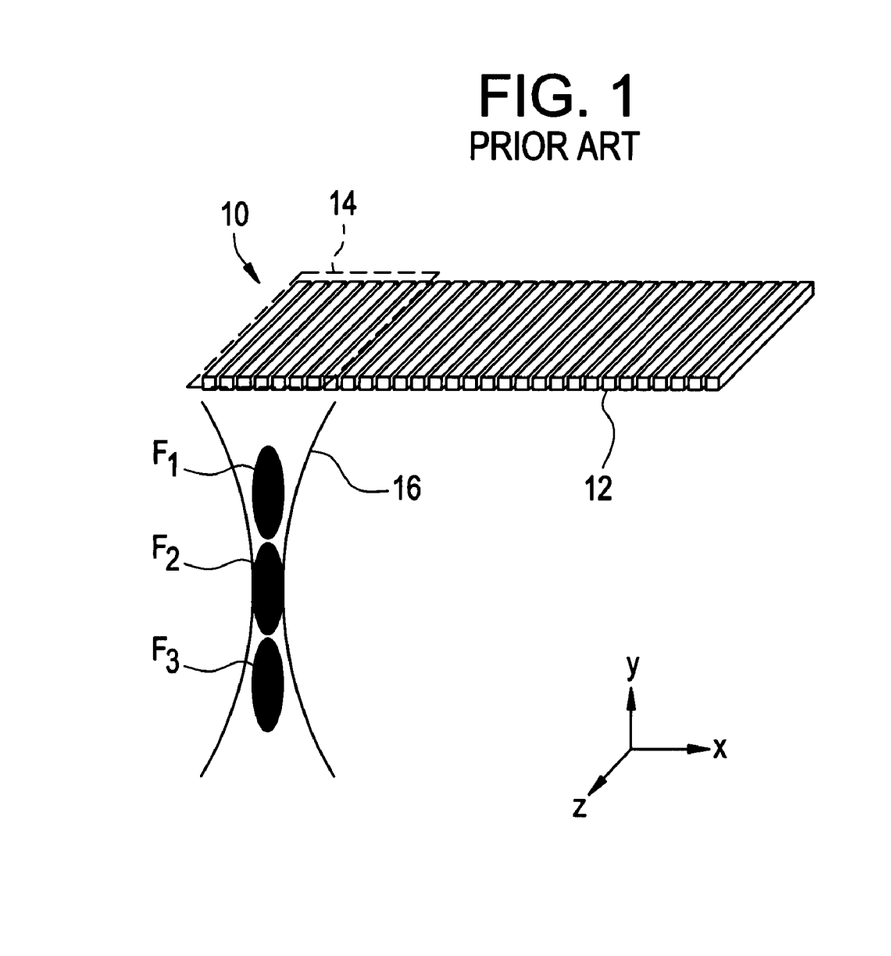
FIG. 1 is a schematic illustration of a prior art one-dimensional phased array.
Figure 2:
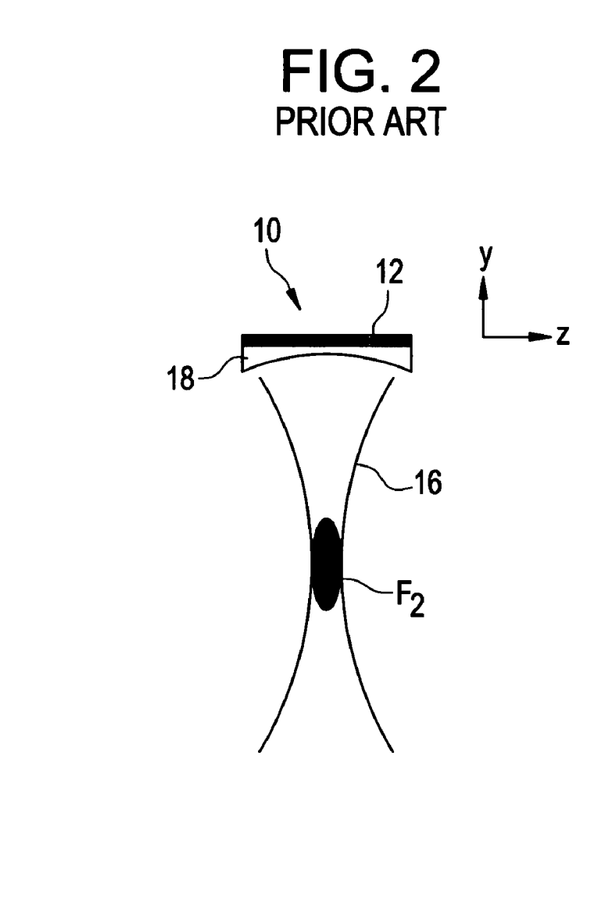
FIG. 2 is a schematic side elevational view of the one-dimensional phased array of FIG. 1.

Referring initially to FIGS. 1 and 2, a prior art one-dimensional phased array is designated generally at numeral 10. As seen in FIG. 1, phased array 10 includes a linear array of transducers 12 extending in an X direction (i.e., an azimuthal direction). Each transducer 12 is typically one quarter to several wavelengths in width in the azimuthal direction and tens or hundreds of acoustic wavelengths in width in a Z direction (i.e., an elevational direction).

Array 10 is configurable to define a plurality of apertures 14 by electronically addressing and subsequently firing a group of elements. For illustrative purposes a single aperture 14 is identified by the indicated region of FIG. 1. Aperture 14 of array 10 typically has a fixed dimension in the Z direction equal to the elevational width of the transducers 12 and a variable dimension in the X direction directly related to the number of transducers 12 activated during the particular shot. Aperture 14 is configured and adapted to produce a scanning beam 16 against a test piece to be analyzed (not shown). Due to the fixed size and focal properties of transducers 12 in the elevation direction, scanning beam 16 emitted from aperture 14 has fixed focal properties in the Z direction. Given that the aperture size and focal characteristics can be modified in the azimuthal and/or elevation directions, the scanning beam 16 emitted from aperture 14 has variable focal properties in the X direction.

Note that the focal properties are described as being discretely separate in the azimuth-depth and elevation-depth planes for the purpose of describing the benefits of the invention. It is recognized and intended that the azimuthal and elevation properties act together to form focal properties that are actually three dimensional in nature. The focal properties are considered separate from the standpoint of being able to significantly modify them in an electronic sense in the azimuth-depth and elevation-depth planes.

As seen in FIG. 2, each transducer 12 can be provided with a lens 18 configured and dimensioned for focusing beam 16 in elevation against the test material.

Accordingly, in use, aperture 14 of array 10 can only be sized and focal laws only applied in the X direction. In addition, as seen in FIGS. 1 and 2, array 10 is configured for electronic scanning in the X direction and is able to produce various focal zones "$F_{1-3}$" in the Y direction while lens 18 of each transducer 12 can only focus scanning beam 16 in the Z direction to produce one focal zone "$F_2$" in the Y direction.

In other words, due to the configuration and dimension of transducers 12, beam 16 can be formed in the X-Y plane (i.e., the azimuth-depth plane) to provide multiple focal zones "$F_{1-3}$" in the X-Y plane. Since beam 16, in the Z-Y plane (i.e., the elevation-depth plane), is fixed based on the physical characteristics of array 10 (i.e., lens, focal length, frequency, etc.) the characteristics of beam 16, in the Z direction, can only be optimized for a single depth barring physical changes to array 10. Accordingly, a single focal zone $F_2$ is produced in the Z-Y plane.

As will be described in greater detail below, the present disclosure relates to a phased array including a plurality of miniature ultrasonic transducers arranged in a two-dimensional rectilinear grid pattern. The transducers are individually addressable and therefore electronically controllable using phased array beam forming/imaging systems. The pattern of the transducers and the focal characteristics of the array are chosen to provide the ability to use dynamic electronic beam forming and aperture control in both the azimuthal and elevation directions to produce uniform focal characteristics throughout the entire volume of the material that is to be tested and/or inspected.

In addition, the two-dimensional phased array, according to the present disclosure, permits the use of a large array of transducers to develop foci over a significant range of depths. This offers improvement in range and resolution over conventional ultrasonic phased arrays and improvement in inspection and/or testing speed, the ability to correct for the surface geometry of the test material, and the ability to use a single two-dimensional phased array probe as opposed to multiple conventional probes.

Application of the two-dimensional phased array to a volumetric component and/or material to be tested, enables acquisition of focal characteristics, equivalent to those produced by spherically focused transducers. Application of the two-dimensional phased array also enables electronic correction for one and two dimensional surface curvatures or other complex geometry on the material to be tested.

Figure 3:
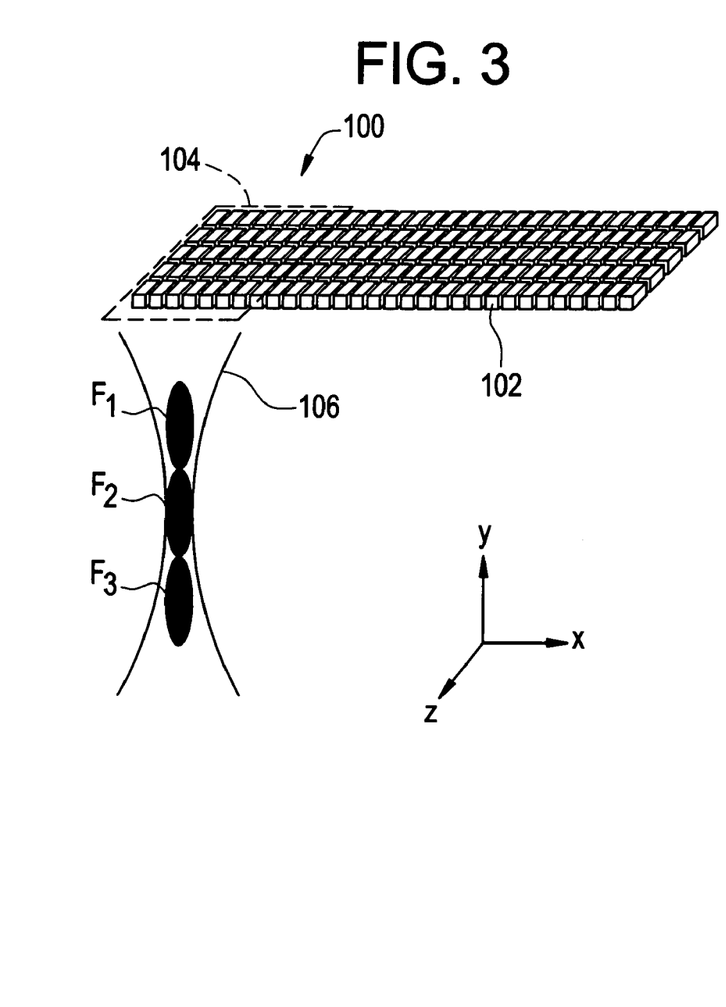
FIG. 3 is a schematic illustration of a two-dimensional phased array in accordance with an embodiment of the present disclosure.
Figure 4:
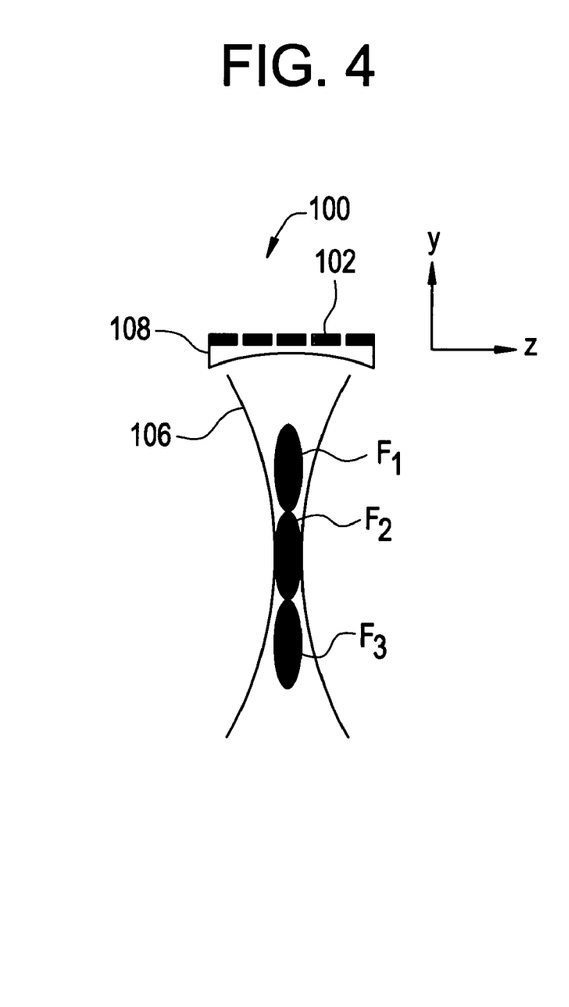
FIG. 4 is a schematic side elevational view of the two-dimensional phased array of FIG. 3.

With reference to FIGS. 3-9, and initially with particular reference to FIGS. 3 and 4, a two-dimensional phased array, in accordance with an embodiment of the present disclosure, is designated generally at 100. Two-dimensional phased array 100 includes a rectilinear array of ultrasonic elements 102, preferably, piezoelectric transducers and the like. Transducers 102 extend in both an X direction (i.e., an azimuthal direction) and a Z direction (i.e., an elevation direction). Illustrative examples of transducers 102 are disclosed in U.S. Pat. No. 4,890,268.

Each transducer 102 can be individually wired and connected, through a multiplexer (not shown), to independent pulser/receiver/beamformer channels such that each transducer 102 can be electronically modulated in time, frequency, phase, amplitude, bandwidth, etc. Accordingly, a group of transducers 102 can be used to form an aperture 104 as identified by the indicated region of FIG. 3. Aperture 104 of array 100 has a variable dimension in the Z direction which is directly related to the number of transducers 102 activated in the Z direction during a particular scan and a variable dimension in the X direction which is directly related to the number of transducers 102 activated in the X direction during the particular scan.

It is envisioned that phased array 100 can be formed from a collection of discrete ultrasonic transducers 102, or, as is customary, phased array 100 can be composed of a single mechanical entity including a plurality of elements each constructed as separate ultrasonic entities and each being at least electrically independent, and desirably not mechanically independent.

By applying modulation to individual transducers 102 of aperture 104, an ultrasonic scanning beam 106 can be formed that has the ability to interrogate a portion of a test material to be analyzed (not shown). For example, transducers 102 can be modulated in such a way that scanning beam 106 can be steered and focused as needed.

In order to form apertures 104 of significant size, the dimensions of transducers 102 in the Z or elevation direction of array 100 may be larger than the dimensions of transducers 102 in the X or azimuth direction. Accordingly, each transducer 102 can have a dimension in the X or azimuth direction which is on the order of about 0.5 acoustic wavelengths to about 7 acoustic wavelengths. It is further envisioned that each transducer 102 can have a dimension in the Z or elevation direction which is on the order of about 0.5 acoustic wavelengths to about 20 acoustic wavelengths.

Figure 6:
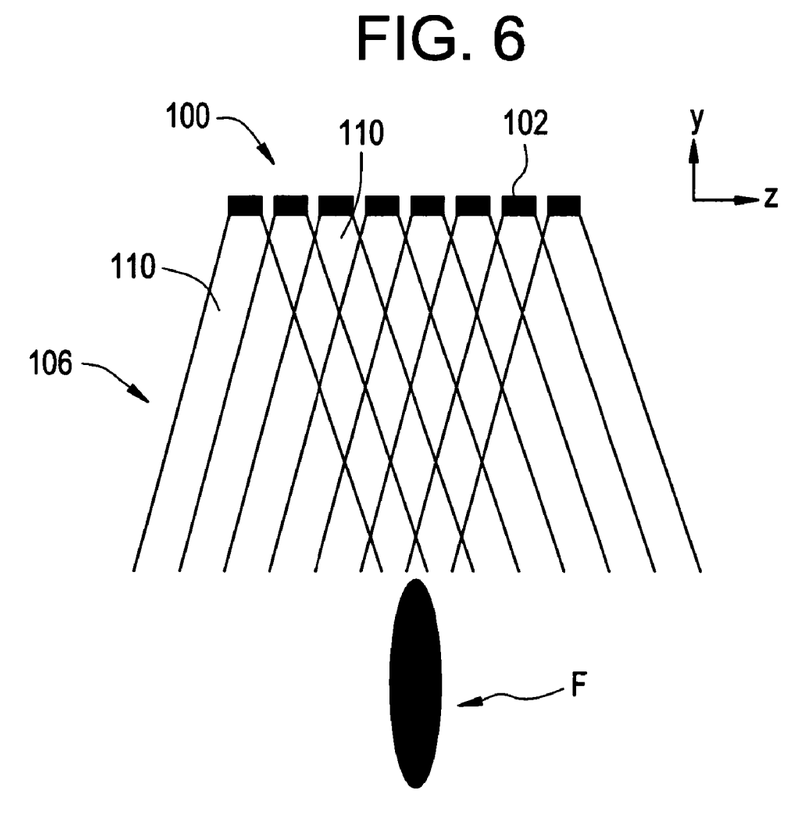
FIG. 6 is an enlarged schematic side elevational view of the two-dimensional phased array of FIGS. 3 and 4 illustrating the production of multiple focal zones.

As seen in FIG. 6, the relatively small dimension of transducers 102 in the Z direction allows for a respective divergent ultrasonic beam 110 to be emitted from each individual transducer 102. Accordingly, the sound field produced by each transducer 102 interacts with the sound field produced by other transducers 102 in aperture 104.

Since transducers 102 have a larger dimension in the Z direction a narrower ultrasonic beam 110 is emitted therefrom. Accordingly, transducers 102 have increased divergence as compared to conventional transducers. However, the divergence of these transducers may not be large enough to encompass the focal point of interest. As such, each transducer 102 can be directed to the approximated location at which the scan is to take place. Each transducer 102 can be directed by using a focusing lens 108, as will be described in greater detail below, or by curving array 100 in the elevational plane.

As seen in FIG. 4, a focusing lens 108 can be provided which extends across aperture 104 in the Z direction. While lens 108 is shown as extending across all the transducers 102 in the Z direction, it is envisioned and within the scope of the present disclosure to provide a respective lens 108 for each respective transducer 102 or to provide a lens 108 which extends across more than one or multiple transducers 102.

Accordingly, in use, aperture 104 of array 100 can be sized and focal laws applied in both the X and Z directions. In addition, as seen in FIGS. 3 and 4, array 100 is configured for electronic scanning in the X direction and is able to produce focal points and/or zones "$F_{1-3}$" at varying levels and/or depths in both the X-Y and Z-Y planes.

Two-dimensional rectilinear phased array 100 offers an improvement over one-dimensional linear array 10 in that phased array 100 is separated and/or divided into a plurality of discrete transducers 102 extending in both the X and Z directions. Accordingly, formation of scanning beam 106 can take place in both the X-Y plane (i.e., the azimuth-depth plane) and the Z-Y plane (i.e., the elevation-depth plane). This enables three-dimensional control of scanning beam 106 with respect to focal depth, steering angle, and focal geometry.

Control of aperture 104 also contributes to the formation of scanning beam 106. Aperture 104 of array 100 can be selected by multiplexing scanning beam 106 to connect phasing channels to specific transducers 102 of array 100. Given the two-dimensional rectilinear pattern of transducers 102, the size of aperture 104 can be controlled and/or adjusted in both the X and Z directions. Furthermore, the shape of aperture 104 can be approximated to a rectangle, square, circle, semi-circle, oval, triangle, trapezoid, rhombus and any combination thereof by simply activating selected transducers 102.

In view of the above features, array 100 enables control of the size and/or shape of scanning beam 106 as well as the number of focal zones produced in the X-Y plane and the Z-Y plane.

Figure 5:
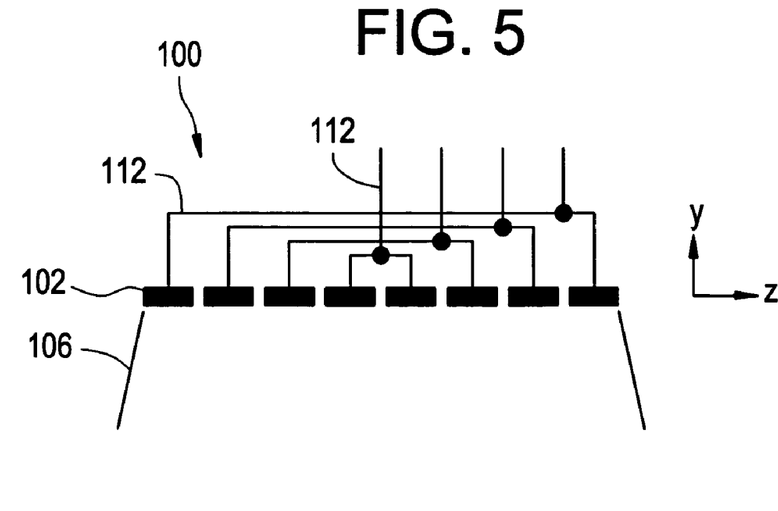
FIG. 5 is a schematic side elevational view of a 1.5 dimensional phased array architecture illustrating the electrical connection between pairs of transducer elements which are symmetric about the azimuthal center line of the array.

In one embodiment of the present disclosure, as seen in FIG. 5, the elevation dimension is only required to focus and is not necessary to provide steering of scanning beam 106 in the Z-Y plane. Accordingly, it is possible to construct array 100 such that the rows of transducers 102 are positioned symmetrically about a central axis of array 100 extending in the X direction and that symmetrical transducer pairs 102 are connected electrically in parallel to a single electronic channel (not shown) by leads 112. This is beneficial in that it reduces the number of active beam former channels by a factor of two. Conversely, given the maximum number of beam former channels available in a given system, it increases the size of aperture 104 that can be generated by the same factor of two. An array constructed as such is termed a one point five dimensional (1.5D) array. The use of a 1.5D wiring architecture reduces the overall active channel count needed to produce apertures 104 of sufficient size to generate the focal properties needed for the test.

In an additional embodiment, array 100 can be pre-focused in the Z direction. This can be accomplished by adding an acoustic lens (not shown) to transducers 102 in the Z direction, or by physically curving transducers 102. This effectively allows the size of transducers 102, in the Z direction, to be increased because the element is nominally focused and steered in the direction that it will be required to operate. This fabrication technique also allows for the construction of apertures 104 which are larger then conventional apertures using a given number of beam-former channels.

Figure 7:
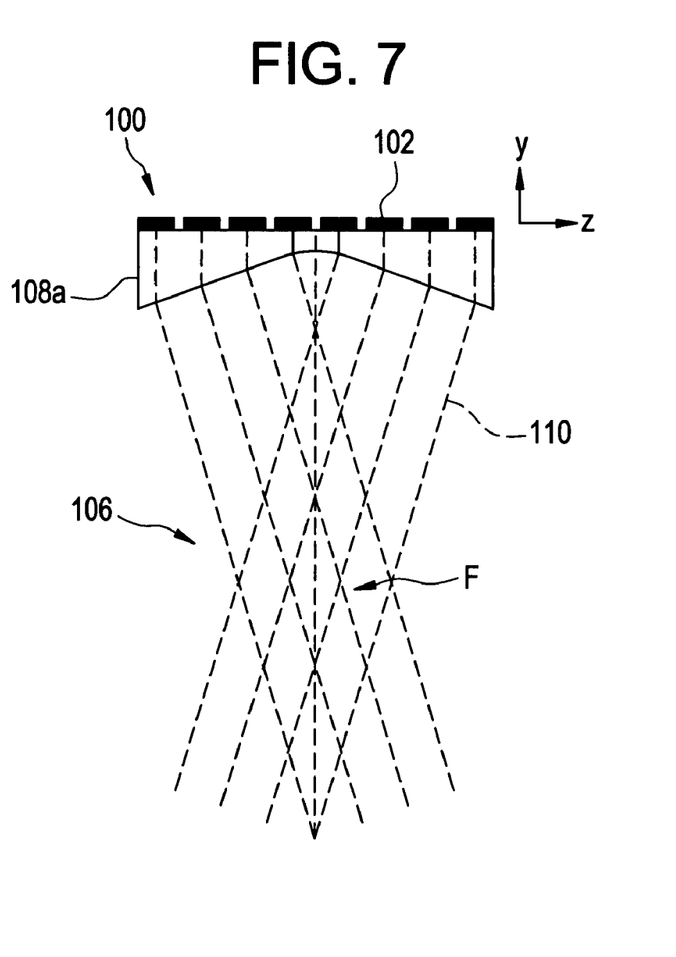
FIG. 7 is an enlarged schematic side elevational view of the two-dimensional phased array of FIG. 6 including a focusing lens having a plano-concave and/or a plano-convex portion for producing a constant F/D ratio.
Figure 8:
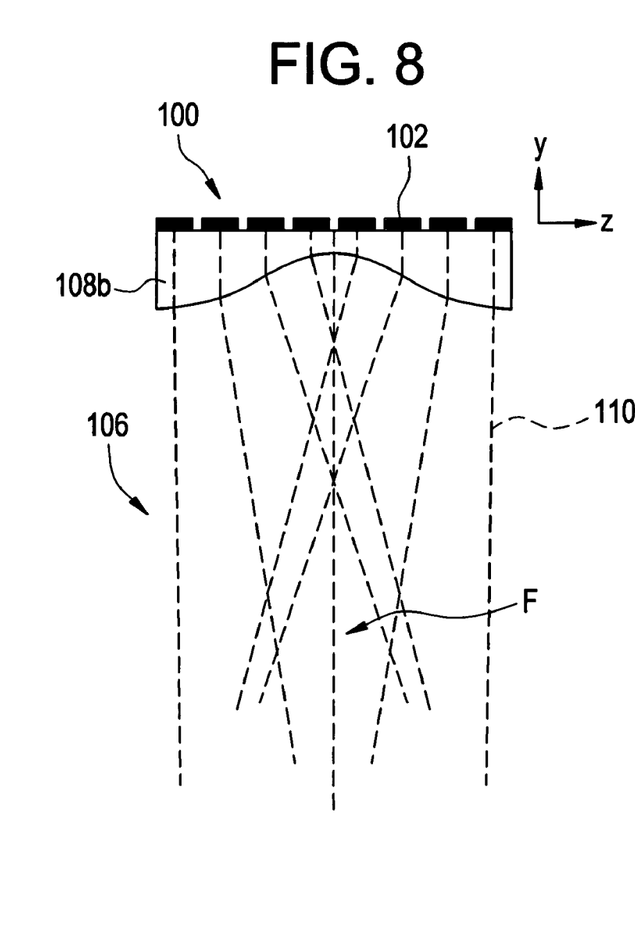
FIG. 8 is an enlarged schematic side elevational view of the two-dimensional phased array of FIG. 6 including a focusing lens having a plano-concave and/or a plano-convex portion for producing an increasing F/D ratio.
Figure 9:
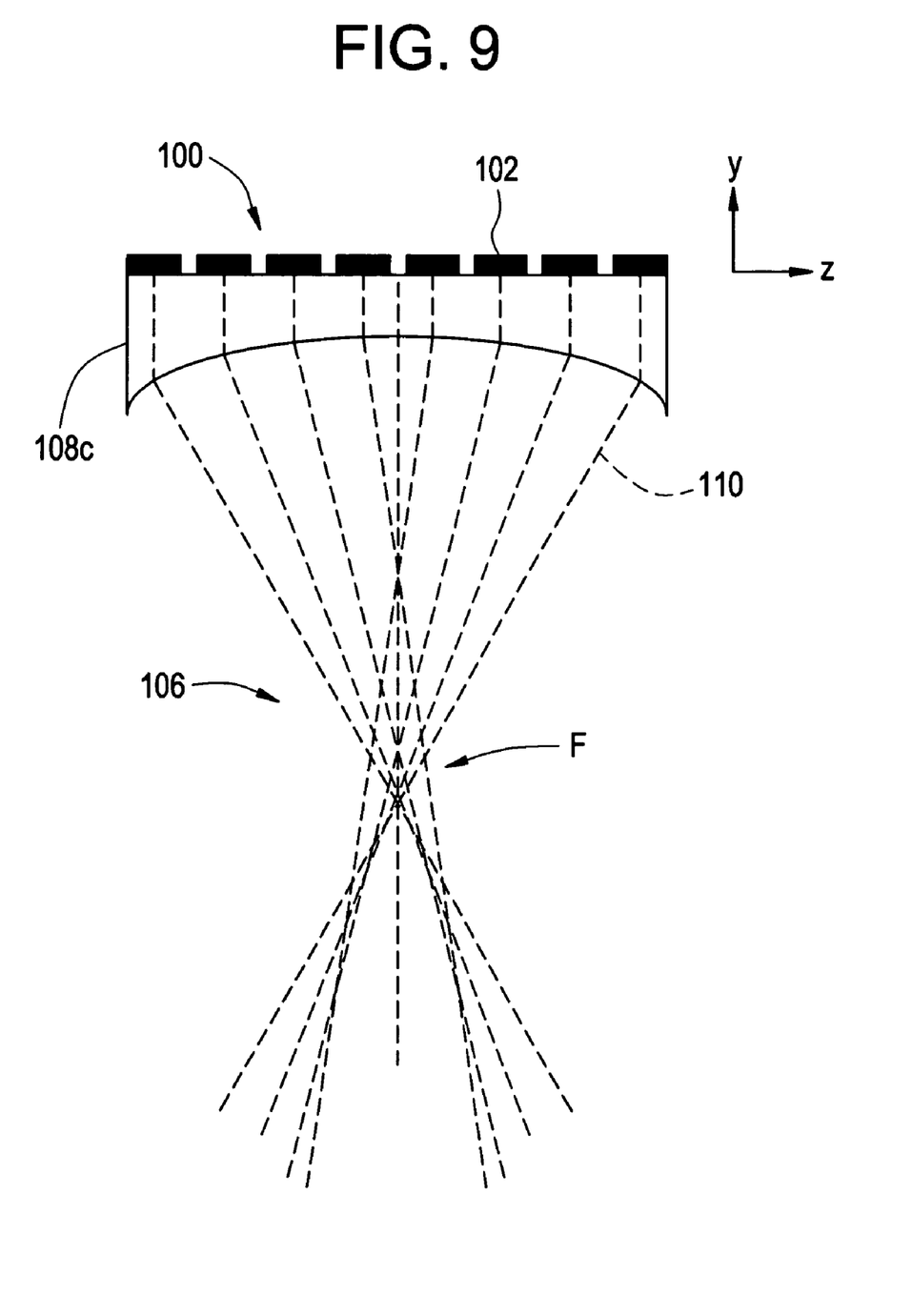
FIG. 9 is an enlarged schematic side elevational view of the two-dimensional phased array of FIG. 6 including a focusing lens having a plano-concave and/or a plano-convex portion for producing a decreasing F/D ratio.

In yet another embodiment, the focal geometry of transducer 102 and/or lens 108 is prescribed independently for each row of transducers 102. For example, transducer 102 and/or lens 108 can have a concave, a convex, a linear and/or a plano-concave shape as shown in FIGS. 7, 8 and 9. This also allows the size of transducers 102, in the Z direction, to be increased due to the nominal steering and focusing of each row in the Z direction to its optimal point of operation. This increases the size of aperture 104 given a finite number of beam forming channels. While lens 108 is shown as extending across all transducers 102 in the Z direction, it is envisioned and within the scope of the present disclosure to provide a respective lens 108 for each respective transducer 102 or to provide a lens 108 which extends across more than one or multiple transducers 102.

In an additional embodiment, the total number of transducers 102 is much larger than the number of beam-forming channels. Accordingly, transducers 102 are connected to the beam-forming channels through a multiplexer (not shown). This allows aperture 104 to be electronically scanned through transducers 102, replacing the necessity for mechanical scanning.

With reference to FIGS. 7-9, illustrations of various ultrasonic scanning beams producing characteristic focal zones, in accordance with embodiments of the present disclosure are shown. As seen in FIG. 7, array 100 includes a plano-concave lens 108a configured and dimensioned to produce a constant F/D ratio over the operating range of array 100. In particular, lens 108a is configured and dimensioned to manipulate ultrasonic beams 110 to produce uniform sized focal zones "F" in scanning beam 106. As will be appreciated, a F/D ratio may be defined as a ratio of the focal length of the plano-concave lens to its diameter. It describes the basic geometric architecture of the plano-concave lens, which affects its physical size, its design and its electrical performance.

As seen in FIG. 8, array 100 includes a plano-concave lens 108b configured and dimensioned to produce an increasing F/D ratio over the operating range of array 100. In particular, lens 108b is configured and dimensioned to manipulate ultrasonic beams 110 to produce increasing sized and/or diverging focal zones "F" in scanning beam 106.

As seen in FIG. 9, array 100 includes a plano-concave lens 108c configured and dimensioned to produce a decreasing F/D ratio over the operating range of array 100. In particular, lens 108c is configured and dimensioned to manipulate ultrasonic beams 110 to produce decreasing sized and/or converging focal zones "F" in scanning beam 106.

While FIGS. 7-9 illustrate plano-concave lenses 108a-108c, it is envisioned and within the scope of the present disclosure that plano-concave lenses 108a-108c can be replaced with plano-convex lenses or similarly shaped elements as is consistent with standard practices of ultrasonic transducer design.

Use of a lens 108, preferably a multi-focus lens, such as, for example, a plano-concave lens, on transducers 102, enables pre-focusing of the elevation rows of transducers 102 in order to allow a larger elevation pitch, and to thereby reduce the overall active channel count needed to produce apertures 104 of sufficient size to generate the focal properties needed for the inspection and/or testing. It is envisioned that array 100 can be provided with lens 108, having multiple sections of concave, linear, and convex shape, that can be used in combination with a corresponding azimuthal electronic focus to generate lenses that are comparable to the spherical, axicon and toroidal focal geometries of single element conventional transducers.

While the above disclosure is related to a phased array having a rectilinear pattern/arrangement, it is envisioned and within the scope of the present disclosure to provide for a phased array having a non-rectilinear pattern/arrangement, such as, for example, staggered, stepped, off-set and the like. Furthermore, the elements may not be rectangular in shape, being round, elliptical, trapezoidal, or triangular. Finally, the above disclosure describes two dimensional transducers whose elements are spaced continuously and in a close packed fashion. It is also envisioned that in order to maximize the aperture size, the transducers may be arranged with relatively large spaces between them, or in a sparse fashion.

While the preferred forms and embodiments of the invention have been illustrated and described herein, it will be apparent to those of ordinary skill in the art that various changes and modifications may be made without deviating from the inventive concepts and spirit of the invention as set forth above, and it is intended by the appended claims to define all such concepts which come within the full scope and true spirit of the invention.

What is claimed is:

1. A method for performing an ultrasonic volumetric inspection of a backscattering material, comprising the steps of:
   providing a two-dimensional ultrasonic phased array, the phased array includes a plurality of ultrasonic elements arranged in a two-dimensional rectilinear grid pattern extending in azimuthal and elevational directions, each ultrasonic element has an overall elevational dimension that is greater than its overall azimuthal dimension, the two-dimensional ultrasonic phased array configured with no more than one focusing lens wherein said focusing lens is curved soley in the elevational direction to direct said each ultrasonic element in each respective column to a desired elevational location;
   applying modulation to said each ultrasonic elements in both the azimuthal and elevational directions to form an ultrasonic scanning beam configured to produce focal zones in an azimuth-depth plane and an elevational-depth plane; and
   interrogating at least a portion of the backscattering material.

2. The method according to claim 1, wherein interrogating at least a portion of the backscattering material comprises configuring the no more than one focusing lens to provide a desirable F/D ratio to focus the ultrasonic elements of the ultrasonic phased array at desirable depths, and directing the ultrasonic scanning beam via the no more than one focusing lens.

3. The method according to claim 1, wherein the ultrasonic elements are electronically modulated in at least one of time, frequency, phase, amplitude, bandwidth or combinations thereof.

4. The method according to claim 1, further comprising the step of:
   manipulating the ultrasonic elements in at least one of the azimuthal and elevational directions to produce focal zones at various levels of the backscattering material.

5. The method according to claim 1, wherein at least one of the ultrasonic elements is capable of emitting a divergent ultrasonic beam.

6. The method according to claim 5, further comprising the step of forming discrete divergent ultrasonic scanning beams in the azimuthal and elevational directions.

7. The method according to claim 6, further comprising the step of forming the discrete divergent ultrasonic scanning beams in an azimuth-depth plane.

8. The method according to claim 6, further comprising the step of forming the discrete divergent ultrasonic scanning beams in an elevation-depth plane.

9. The method according to claim 1, wherein each ultrasonic element includes an aperture and wherein the method further comprises the step of independently adjusting the aperture of selected ultrasonic elements in two-dimensions.

10. The method according to claim 1, further comprising the step of focusing selected ultrasonic elements in two-dimensions.

11. The method according to claim 1, wherein the step of interrogating at least a portion of the backscattering material includes taking a sequence of shots to produce a uniform beam pound field.

12. The method according to claim 1, further comprising the step of manipulating the ultrasonic scanning beam in azimuth, elevation and depth directions to produce at least one of a uniform and specific scanning beam for every point inside a volume of the backscattering material.

13. The method according to claim 12, wherein the step of manipulating is accomplished electronically.

14. The method according to claim 1, wherein the two-dimensional phased array includes aperture control.

15. The method according to claim 14, wherein the aperture control provides control of an aperture of the two-dimensional phased array in at least one of the azimuth and elevational directions to provide at least one of a uniform and specific scanning beam at every point inside a volume of the material.

16. The method for performing an ultrasonic volumetric inspection of a material according to claim 1, wherein providing the two-dimensional ultrasonic phased array configured with no more than one focusing lens curved solely in the elevational direction comprises curving the entire two-dimensional ultrasonic phased array solely in the elevational plane to form a focusing lens arrangement corresponding to a single focusing lens.

17. A two-dimensional ultrasonic phased array for inspecting a backscattering material, the two-dimensional phased array, comprising:

a plurality of ultrasonic elements ranged in a two-dimensional rectilinear grid pattern extending in an azimuthal and elevational direction, each ultrasonic element is individually addressable and controllable to manipulate the formation of an ultrasonic scanning beam in both the azimuthal and elevational directions and to produce focal characteristics throughout the volume of the backscattering material, wherein each ultrasonic element has an overall elevational dimension that is greater than its overall azimuthal dimension, and further wherein the two-dimensional rectilinear grid pattern is configured with no more than one focusing lens, wherein said focusing lens is curved solely, in the elevational direction to direct each ultrasonic element in each respective column to a desired elevational location.

18. The two-dimensional ultrasonic phased array of claim 17, wherein the ultrasonic elements are electronically modulated in at least one of time, frequency, phase, amplitude, bandwidth or combinations thereof.

19. The two-dimensional ultrasonic phased array of claim 17, wherein the ultrasonic elements produce focal zones at various levels in an azimuth-depth plane.

20. The two-dimensional ultrasonic phased array of claim 19, wherein the ultrasonic elements produce focal zones at various levels in an elevation-depth plane.

21. The two-dimensional ultrasonic phased array of claim 17, wherein a selected number of ultrasonic elements define an aperture.

22. The two-dimensional ultrasonic phased array of claim 21, wherein the ultrasonic elements selected define a shape for the aperture.

23. The two-dimensional ultrasonic phased array of claim 17, wherein the ultrasonic elements have a dimension in the azimuthal direction of about 0.5 to about 7 acoustic wavelengths.

24. The two-dimensional ultrasonic phased array of claim 23, wherein the ultrasonic elements have a dimension in the elevation direction of about greater than 0.5 to about 20 acoustic wavelengths.

25. The two-dimensional ultrasonic phased array of claim 17, wherein each ultrasonic element is configured to emit a divergent ultrasonic scanning beam.

26. The two-dimensional ultrasonic phased array of claim 25, wherein discrete divergent ultrasonic scanning beams are formed in the azimuthal and the elevational directions.

27. The two-dimensional ultrasonic phased array of claim 26, wherein discrete divergent ultrasonic scanning beams are formed in an azimuth-depth plane.

28. The two-dimensional ultrasonic phased array of claim 27, wherein the discrete divergent ultrasonic scanning beams formed in the azimuth-depth plane define focal zones in the azimuth-depth plane.

29. The two-dimensional ultrasonic phased array of claim 28, wherein discrete divergent ultrasonic scanning beams are formed in an elevation-depth plane.

30. The two-dimensional ultrasonic phased ray of claim 29, wherein the discrete divergent ultrasonic scanning beams formed in the elevation-depth plane define focal zones in the elevation-depth plane.

31. The two-dimensional ultrasonic phased array of claim 17, wherein the ultrasonic elements are placed symmetrically about a central axis of the array extending in the azimuthal direction.

32. The two-dimensional ultrasonic phased array of claim 17, wherein the no more than one focusing lens is configured to provide a desirable F/D ratio to focus the ultrasonic elements of the ultrasonic phased array at desirable depths.

33. The two-dimensional ultrasonic phased array of claim 32, wherein the no more than one focusing lens is further configured and dimensioned to produce one of a constant, an increasing and a decreasing F/D ratio over the operating range of the array.

34. The two-dimensional ultrasonic phased array for inspecting a backscattering material according to claim 17, wherein the no more than one focusing lens curved solely in the elevational direction comprises the entire two-dimensional ultrasonic phased array curved solely in the elevational plane to form a focusing lens arrangement corresponding to a single focusing lens.

35. A two-dimensional ultrasonic phased array for inspecting a backscattering material, the two-dimensional phased ray, comprising:

a rectilinear array of ultrasonic elements extending in an azimuth and an elevation direction, wherein each ultrasonic element is configured to emit a divergent ultrasonic scanning beam which divergent ultrasonic scanning beams combine to form a single ultrasonic scanning beam, wherein the divergent ultrasonic scanning beams formed in an azimuth-depth plane define multiple focal zones in the azimuth-depth plane and wherein divergent ultrasonic scanning beams formed in an elevation-plane define multiple focal zones in the elevation-depth plane, and further wherein each ultrasonic element has an overall elevational dimension that is greater than its overall azimuthal dimension, and further wherein the rectilinear array of ultrasonic elements is configured with no more than one focusing lens, wherein said focusing lens curved solely in the elevational direction to direct each ultrasonic element in each respective column to a desired elevational location.

36. The two-dimensional ultrasonic phased array of claim 35, wherein the ultrasonic elements are electronically modulated in at least one of time, frequency, phase, amplitude, bandwidth or combinations thereof.

37. The two-dimensional ultrasonic phased array of claim 35, wherein the ultrasonic elements have a dimension in the azimuthal direction of about 0.5 to about 7 acoustic wavelengths.

38. The two-dimensional ultrasonic phased array of claim 37, wherein the ultrasonic elements have a dimension in the elevation direction of greater than 0.5 to about 20 acoustic wavelengths.

39. The two-dimensional ultrasonic phased array of claim 37, wherein the no more than one focusing lens is configured and dimensioned to produce one of a constant, an increasing and a decreasing F/D ratio over the operating range of the array.

40. The two-dimensional ultrasonic phased array for inspecting a backscattering material according to claim 35, wherein the no more than one focusing lens curved solely in the elevational direction comprises the entire rectilinear array of ultrasonic elements curved solely in the elevational plane to form a focusing lens arrangement corresponding to a single focusing lens.

* * * * *